(12) United States Patent
Freake et al.

(10) Patent No.: US 11,311,009 B2
(45) Date of Patent: Apr. 26, 2022

(54) INCUBATING ENCLOSURE

(71) Applicant: President and Fellows of Harvard College, Cambridge, MA (US)

(72) Inventors: Jacob Freake, Willimantic, CT (US); Josh Gomes, Somerville, MA (US); Christopher David Hinojosa, Cambridge, MA (US); Daniel Levner, Brookline, MA (US); Doug Sabin, Marblehead, MA (US); Guy Thompson, II, Watertown, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 760 days.

(21) Appl. No.: 15/558,103

(22) PCT Filed: Mar. 17, 2016

(86) PCT No.: PCT/US2016/022928
§ 371 (c)(1),
(2) Date: Sep. 13, 2017

(87) PCT Pub. No.: WO2016/149527
PCT Pub. Date: Sep. 22, 2016

(65) Prior Publication Data
US 2018/0049430 A1 Feb. 22, 2018

Related U.S. Application Data

(60) Provisional application No. 62/135,545, filed on Mar. 19, 2015.

(51) Int. Cl.
*B01L 1/00* (2006.01)
*A01N 1/02* (2006.01)
(Continued)

(52) U.S. Cl.
CPC ......... *A01N 1/0252* (2013.01); *A01N 1/0242* (2013.01); *C12M 41/14* (2013.01); *C12N 5/00* (2013.01)

(58) Field of Classification Search
CPC ........................... A01N 1/0252; A01N 1/0242
See application file for complete search history.

(56) References Cited

U.S. PATENT DOCUMENTS

| 2,317,480 A * | 4/1943 | Peters ................ G05D 23/1919 165/299 |
| 3,076,451 A | 2/1963 | Stoner |

(Continued)

FOREIGN PATENT DOCUMENTS

WO    WO2013086486    6/2013

OTHER PUBLICATIONS

International Search Report and Written Opinion for Application No. PCT/US16/22928, dated Aug. 26, 2016 (13 pages).

*Primary Examiner* — Elizabeth J Martin
*Assistant Examiner* — Nael N Babaa
(74) *Attorney, Agent, or Firm* — Nixon Peabody LLP

(57) ABSTRACT

An incubator assembly includes an incubator enclosure having an internal chamber in which a controlled environment is maintained and which is defined by one or more walls. The incubator assembly further includes a jacket assembly mounted adjacent to at least one of the walls and having an internal airspace in which an internal fluid is enclosed for maintaining a homogenous temperature within the internal chamber. The jacket assembly further has a vent movable between a plurality of positions including an open position in which the internal fluid is allowed to exit the internal airspace into an ambient environment.

13 Claims, 10 Drawing Sheets

(51) Int. Cl.
*C12M 1/00* (2006.01)
*C12N 5/00* (2006.01)

(56) References Cited

U.S. PATENT DOCUMENTS

| | | |
|---|---|---|
| 3,618,734 A | 11/1971 | Khan |
| 4,701,415 A | 10/1987 | Dutton et al. |
| 5,454,368 A * | 10/1995 | Tarulli .................. A61G 11/00 128/202.12 |
| 6,036,633 A | 3/2000 | Hodge |
| 6,210,882 B1 | 4/2001 | Landers et al. |
| 8,647,861 B2 | 2/2014 | Ingber et al. |
| 2001/0007759 A1 | 7/2001 | Wittwer et al. |
| 2010/0203638 A1* | 8/2010 | Adachi .................. C12M 21/08 435/395 |
| 2015/0073204 A1 | 3/2015 | Rapoport |
| 2015/0253561 A1* | 9/2015 | Lee ...................... G02B 21/365 348/80 |
| 2017/0347129 A1* | 11/2017 | Levi ................. H04N 21/42204 |

\* cited by examiner

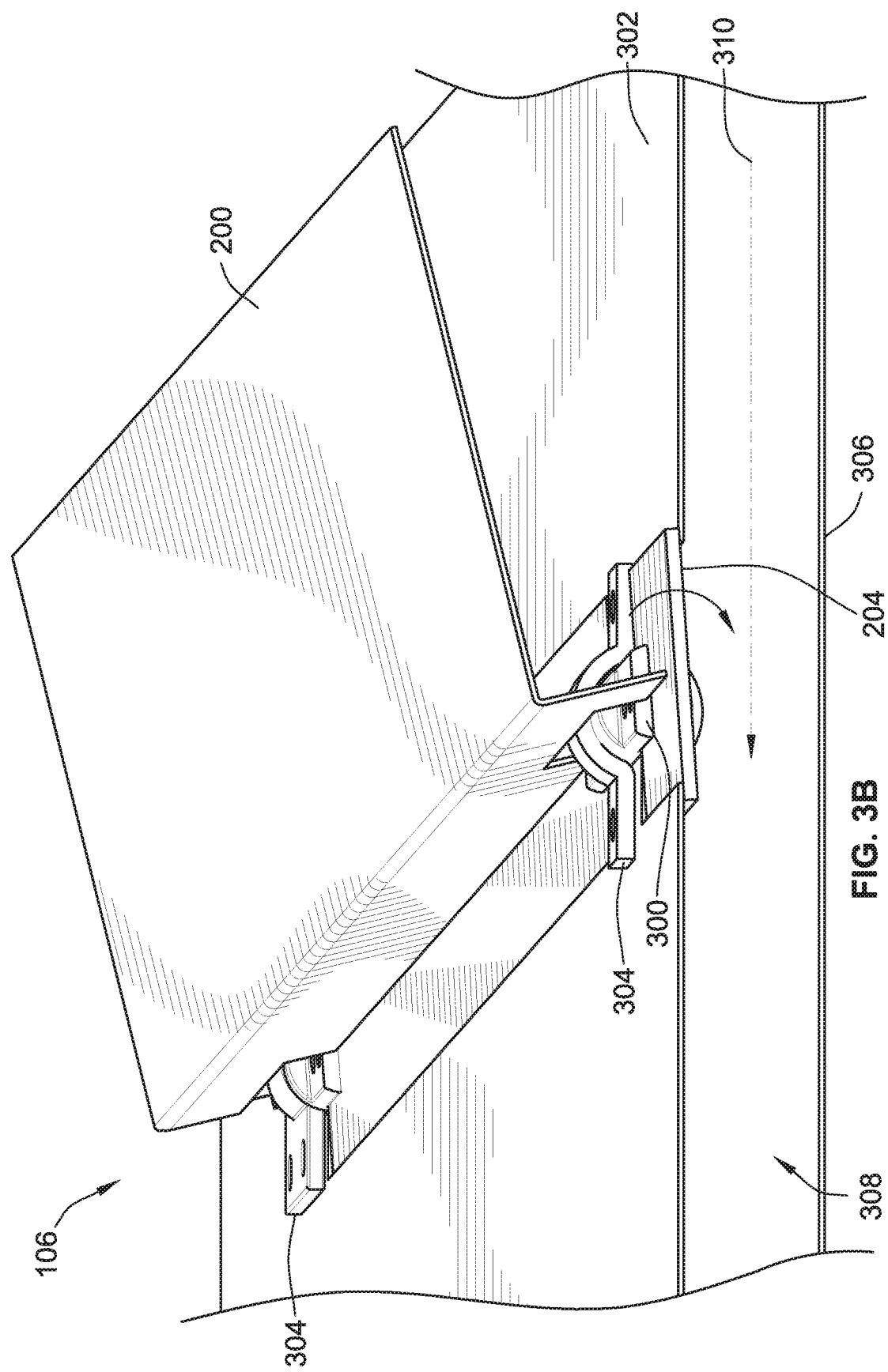

INCUBATING ENCLOSURE

CROSS-REFERENCE TO RELATED APPLICATIONS

This application is a national stage of International Application No. PCT/US2016/022928, filed on Mar. 17, 2016, and titled "Incubating Enclosure," which claims the benefit of and priority to U.S. Provisional Patent Application No. 62/135,545, filed on Mar. 19, 2015, and titled "Incubating Enclosure," each of which are herein incorporated by reference in their respective entireties.

GOVERNMENT SUPPORT

This invention was made with government support under grant no. W911NF-12-2-0036 awarded by U.S. Department of Defense, Advanced Research Projects Agency. The government has certain rights in the invention.

FIELD OF THE INVENTION

The present invention relates generally to incubators and, more particularly, to an incubator assembly with features for cooling and viewing an internal incubator chamber.

BACKGROUND OF THE INVENTION

Commercial incubators are typically used in cell culture to provide a consistent environment where gas concentrations, temperature, and humidity can be controlled. Traditionally, incubators have been designed to accommodate tissue culture dishes and flasks. More recently, tissue culture techniques have changed to include more sophisticated devices that require components such as pumps, valves, optical equipment, etc. These components generate heat that must be removed from the incubator before the temperature increases and, consequently, damages the cultured cells. Present incubators fail to provide features or methods for removing heat that is generated inside the incubator enclosure. Instead, present incubators can only generate heat if the temperature inside the incubator enclosure is too low. As such, one problem with present incubators is that they fail to provide an apparatus or method for cooling temperature inside the incubator enclosure.

Present incubators further serve only as a controlled environment and not typically designed with the user in mind. For example, incubators are usually stacked inside a laboratory, with a typical arrangement having an incubator at knee level and an incubator at chest level. Accordingly, one if a user is required to interact with samples, the user must remove the samples from the incubator and, then, place the samples in a bio hood. The removal from the incubator and the placement in a bio hood can be time-consuming when completing simple actions, such as visual inspection, sampling, or refilling fluid reservoirs. Having to reach into an incubator located at knee level makes user access a frustrating and repeating challenge.

Additionally, access to the incubator enclosure is through a monolithic door. As such, the user and the samples are not protected from each other as they are in the bio hood. Accessing the samples places either or both of the user and the samples at risk from contamination and/or other environmental adverse conditions.

Furthermore, users often wish to quickly glance at their experiments to ensure everything is working properly, e.g., pumps are running, fluid reservoirs have media, etc., but without having to disturb the incubator enclosure environment. Users can glance through a viewing window, however many media components and cells are light sensitive and require protection from ambient light. Present commercial incubators attempt to solve this problem by layering two separate doors, a glass door and a light-impermeable door, each of which can be opened independently. However, an incubator with two such separate doors fails to provide quick viewing access for the user and/or fails to protect the enclosure environment from damaging light.

Therefore, there is a continuing need for providing an incubator assembly that solves the above and other problems.

SUMMARY OF THE INVENTION

According to one aspect of the present invention, an incubator assembly includes an incubator enclosure having an internal chamber in which a controlled environment is maintained and which is defined by one or more walls. The incubator assembly further includes a jacket assembly mounted adjacent to at least one of the walls and having an internal airspace in which an internal fluid is enclosed for maintaining a homogenous temperature within the internal chamber. The jacket assembly further has a vent movable between a plurality of positions including an open position in which the internal fluid is allowed to exit the internal airspace into an ambient environment.

According to another aspect of the invention, a method is directed to cooling an incubator assembly having an incubator enclosure with an internal chamber defined by one or more walls. The incubator assembly further has a jacket assembly mounted adjacent to at least one of the walls and including a vent and an internal airspace containing an internal fluid. The method includes maintaining a controlled environment within the internal chamber of an incubator enclosure. The method further includes circulating the internal fluid within the internal airspace to maintain a homogenous temperature within the internal chamber. In response to a predetermined temperature, the vent is moved from a closed position to an open position to allow (a) hot fluid to exit the internal airspace into an ambient environment and (b) cold fluid to enter the internal airspace.

According to yet another aspect of the invention, an incubator assembly includes an incubator enclosure with an internal chamber defined by a plurality of walls, the internal chamber having a predetermined temperature. The incubator assembly further includes a cooling jacket assembly having a jacket inner shell adjacent to one of the plurality of walls, and a jacket outer shell forming a jacket airspace in-between the jacket inner shell and the jacket outer shell, the jacket airspace containing an internal fluid having a fluid temperature. The cooling jacket assembly further has a vent assembly with a vent vane rotatably mounted to the jacket outer shell on a vane axle, the vent vane being rotatable from a closed position to an open position in response to the predetermined temperature being exceeded. The fluid temperature is lowered by exchanging at least some of the internal fluid with an external fluid while the vent vane is in the open position.

According to yet another aspect of the invention, an incubator assembly includes an incubator enclosure having an internal chamber in which a controlled environment is maintained, the internal chamber being defined by a plurality of walls. The incubator assembly further includes a jacket assembly mounted adjacent to the incubator enclosure and having an internal airspace in which an internal fluid circulates for controllably maintaining a homogenous temperature within the internal chamber. The incubator assembly further includes a sash mounted adjacent to one of the plurality of walls, the sash being movable between a closed position and an open position, the internal chamber being accessible to a user in the open position.

According to yet another aspect of the invention, an incubator assembly includes an incubator enclosure having an internal chamber in which a controlled environment is maintained, the internal chamber being defined by a plurality of walls. The incubator assembly further includes a jacket assembly mounted adjacent to the incubator enclosure and having an internal airspace in which an internal fluid circulates for controllably maintaining a homogenous temperature within the internal chamber. The incubator assembly further includes a viewing window mounted on one of the plurality of walls and having a protective layer that is controllably activated to change between a transparency mode and an opaque mode Additional aspects of the invention will be apparent to those of ordinary skill in the art in view of the detailed description of various embodiments, which is made with reference to the drawings, a brief description of which is provided below.

BRIEF DESCRIPTION OF THE DRAWINGS

FIG. 3B illustrates the vent vane assembly of FIG. 3A in a closed position.

Figure 1:
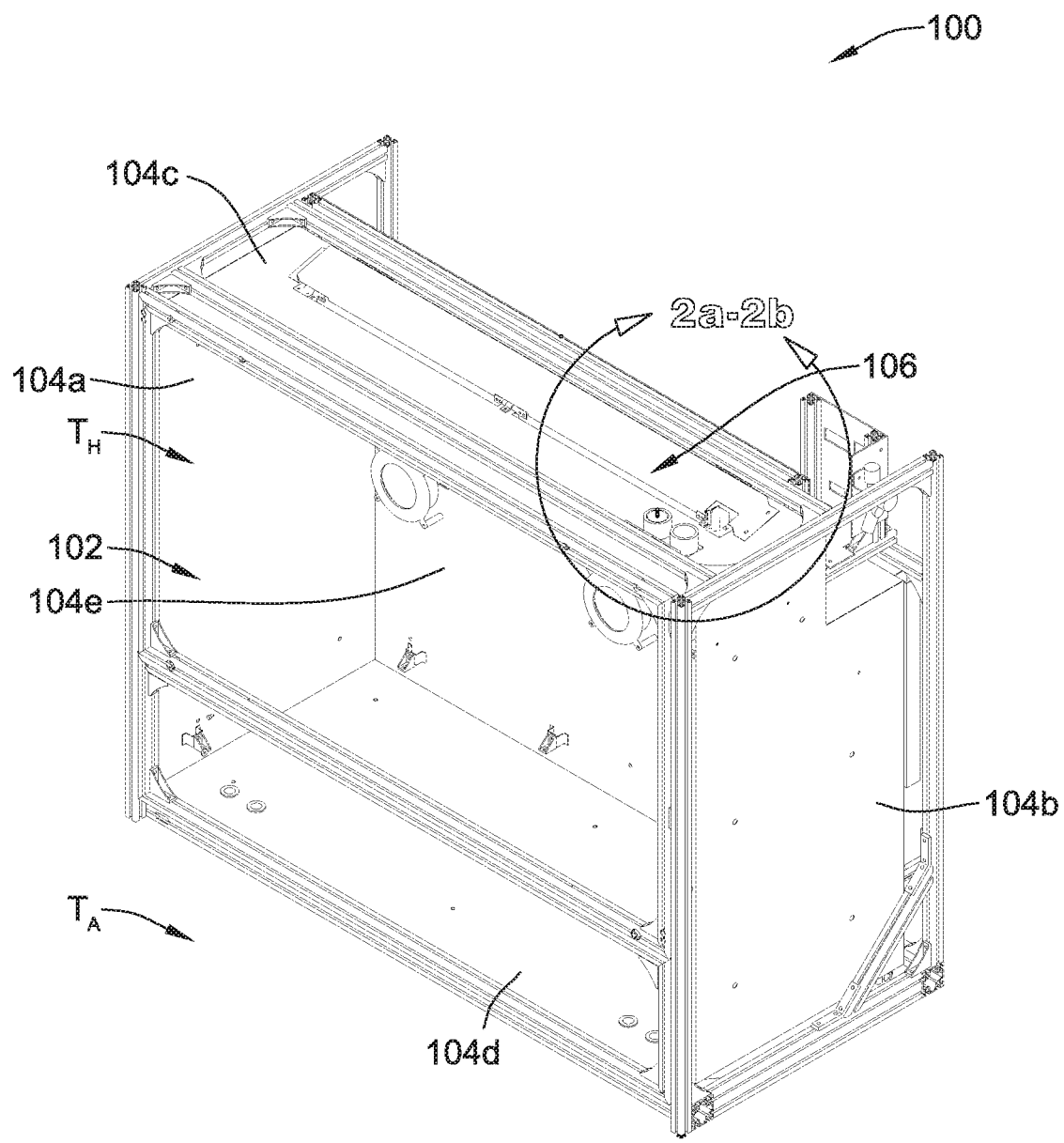
FIG. 1 is an isometric view of an incubator assembly with a vent vane assembly.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

Referring to FIG. 1, an incubator assembly 100 has an internal chamber 102 in which a controlled internal environment, including a desired homogeneous temperature $T_H$, is maintained. The internal chamber 102 is defined by a plurality of walls, including a left wall 104a, a right wall 104b, a top wall 104c, a bottom wall 104d, and a back wall 104e.

To help maintain the homogenous temperature Th, which is typically warmer than an ambient temperature Ta external to the internal chamber 102, the incubator assembly 100 includes a cooling jacket assembly 106 that is capable of removing excess heat by venting out air, water, or other fluids from the jacket assembly 106 and/or injecting new air, water, or other fluids into the jacket assembly 106.

Figure 7:
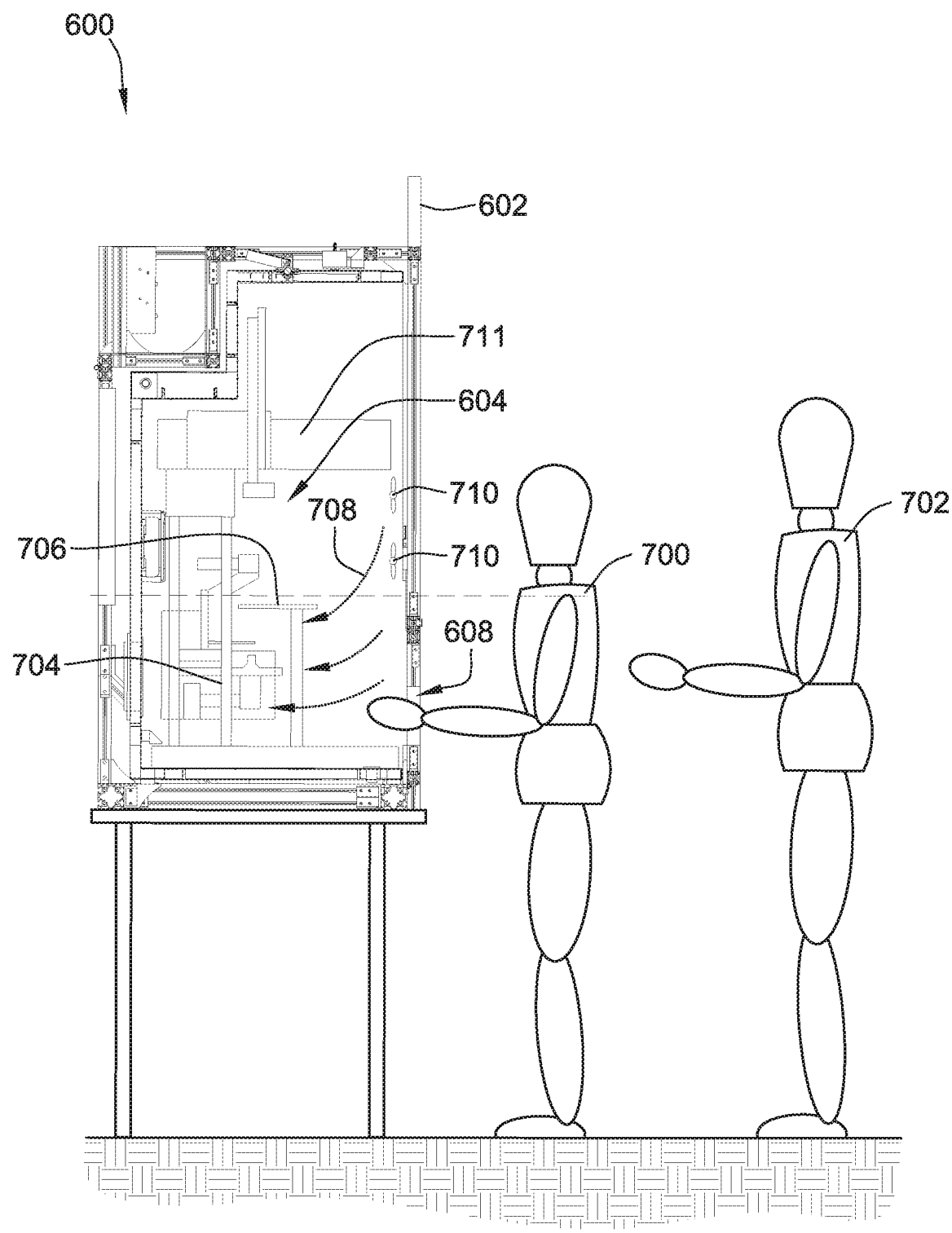
FIG. 7 is a side view of the incubator assembly of FIG. 6.

In one preferred application of the incubator assembly 100, multiple devices that simulate the cell behavior associated with cells, tissues, or organs are placed within the internal chamber 102 along with the various heat-producing devices that are required of them (shown generally as 704 in FIG. 7). Examples of such devices can be found in, for example, WO2013086486 and U.S. Pat. No. 8,647,861, each of which is incorporated by reference in its entirety. The devices include various types of pumps and/or motors to move fluids through micro-channels and to stretch cell-bearing membranes to simulate the physiological effects of expansion and contraction forces that are commonly experienced by cells. They also include various temperature sensors and pressure sensors within or associated with the device. Imaging and optical sensors (e.g., microscopes) are also included to monitor cellular behavior (shown generally as 711 in FIG. 7).

Although, in general, the cooling jacket assembly 106 is used to cool down the temperature in the internal chamber 102, the cooling jacket assembly 106 can also be used to heat up the temperature in the internal chamber 102. Thus, although the exemplary embodiments generally refer to cooling of the internal chamber 102, these exemplary embodiments are non-limiting and can be used in addition to or alternative to heating of the internal chamber 102. The heating of the internal chamber 102 is achieved via the jacket assembly 106 and/or other heating elements.

Because the new fluids brought into the jacket assembly 106 are generally at a cooler fluid temperature $T_F$ than the homogenous temperature $T_H$ of the internal chamber 102, the new fluids act to cool down the internal chamber 102. Often, the cooling of the internal chamber 102 is required because heat-generating components of the incubator assembly 100 change the homogenous temperature $T_H$ to a higher, undesired temperature.

By way of example, it is assumed that in one exemplary embodiment the jacket assembly 106 is an air jacket, the incubator assembly 100 is a mammalian cell culture incubator, and the internal incubator temperature is 37 degrees Celsius. Injecting room-temperature air into the incubator will cool the incubator to a lower desired temperature.

Figure 2A:
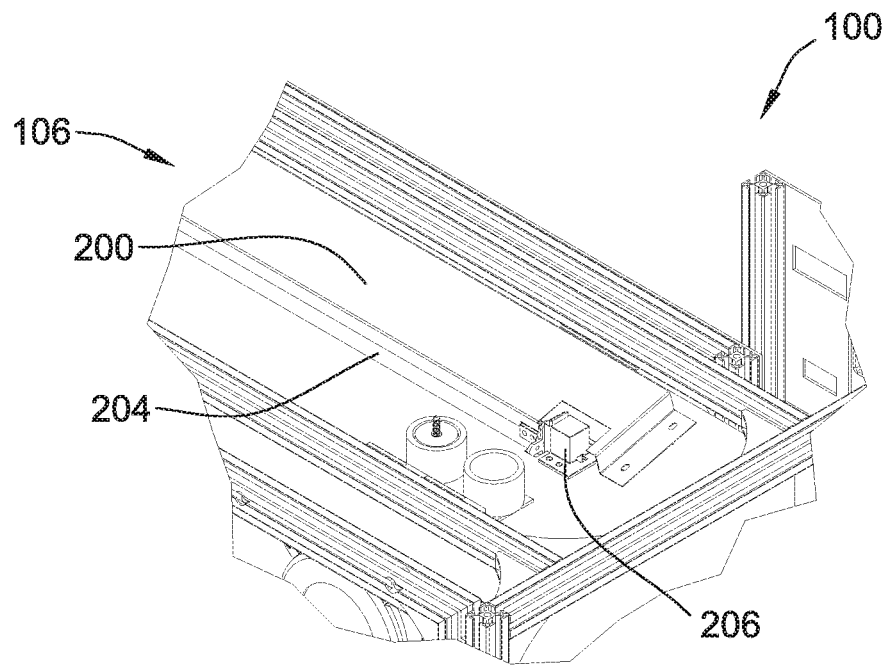
FIG. 2A is a partial isometric view illustrating the vent vane assembly with a vent restrictor panel.
Figure 2B:
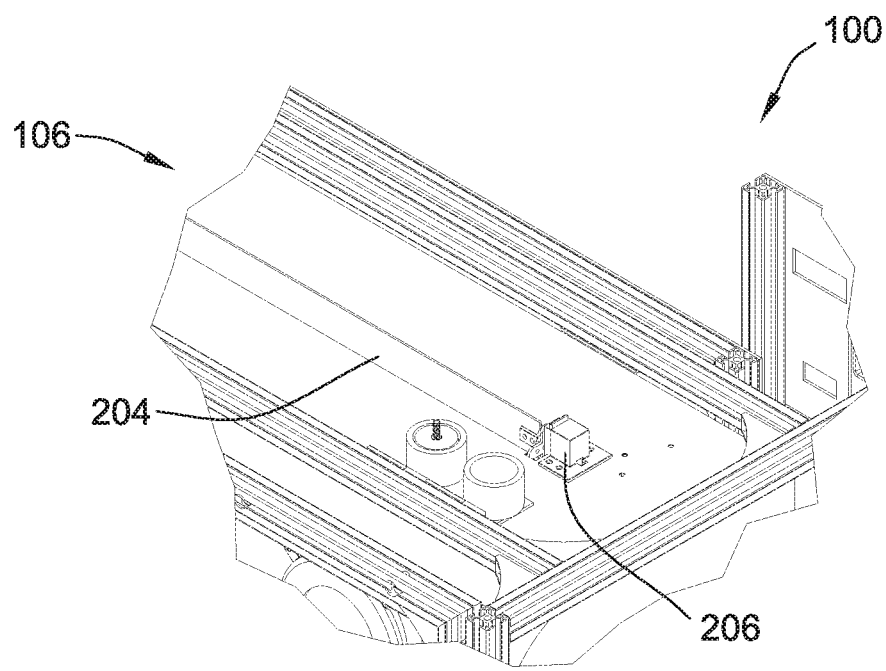
FIG. 2B is a partial isometric view illustrating the vent vane assembly with a vent vane and a drive motor.

Referring to FIGS. 2A and 2B, an enlarged portion of the jacket assembly 106 illustrates a vent restrictor panel 200 mounted external to the top wall 104c and which helps limit motion of a vent vane 204. The vent vane 204 is coupled with a drive motor 206 that, as explained in more detail below, helps to controllably move the vent vane 204 between different positions to change the temperature in the internal chamber 102, e.g., to cool the homogenous temperature $T_H$. The different positions include an open position, a closed position, and one or more intermediate positions.

Figure 3A:
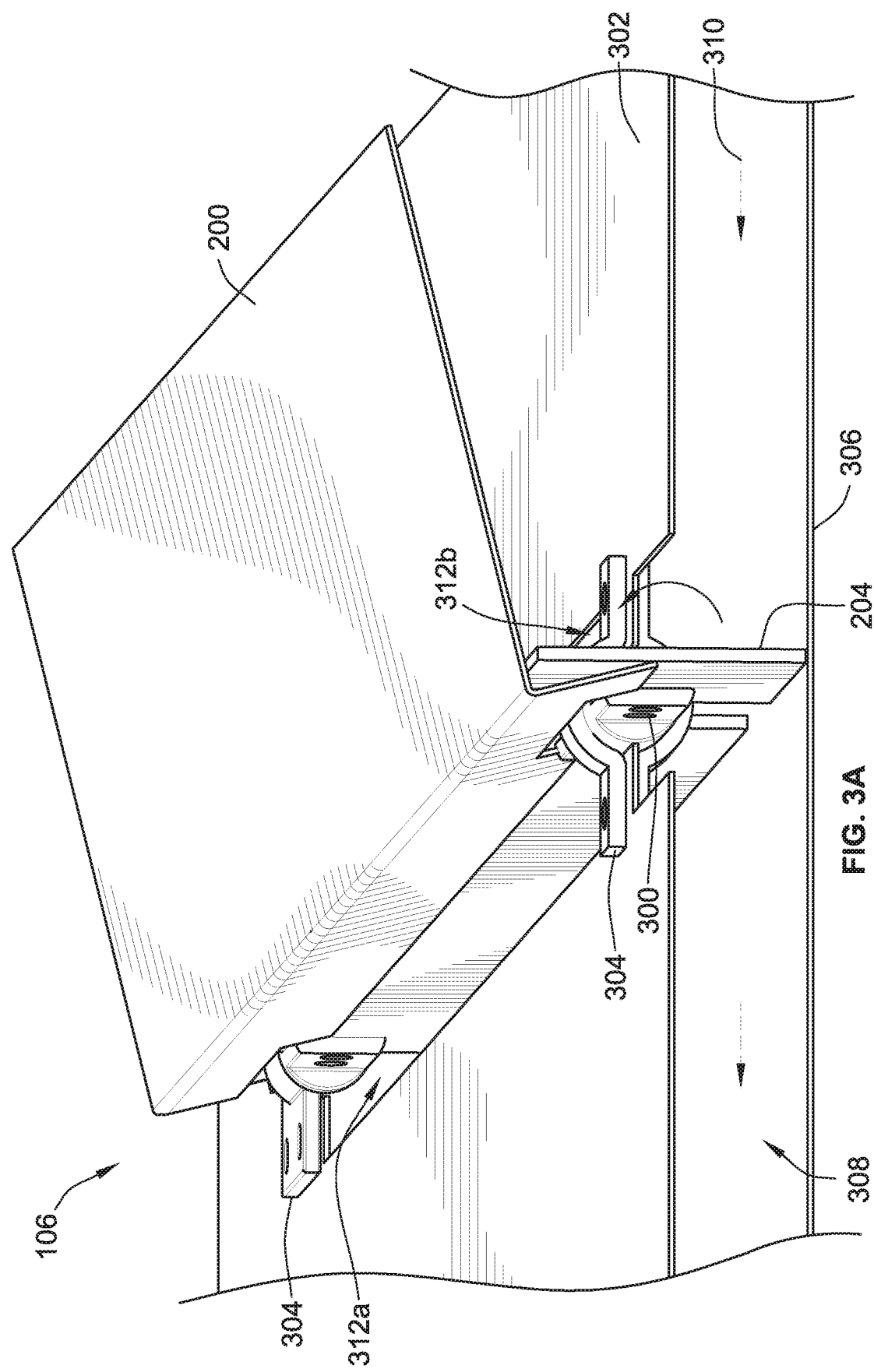
FIG. 3A is a cross-sectional isometric view illustrating the vent vane assembly in an open position.

Referring to FIGS. 3A and 3B, the vent vane 204 is rotatable between the open position (illustrated in FIG. 3A) and the closed position (illustrated in FIG. 3B). The rotation of the vent vane 204 is achieved in part by having the vent vane 204 mounted along a vane axle 300, which is fixed to a jacket outer shell 302 via a pair of axle mounts 304. The jacket outer shell 302 is offset from a jacket inner shell 306, which, together, define an internal airspace 308 in which an internal fluid 310 is circulated for cooling and/or heating the internal chamber 102 of the incubator assembly 100.

The drive motor 206 (illustrated in FIGS. 2A and 2B) causes rotation of the vane axle 300, which, in turn, rotates the vent vane 204 to move between a plurality of positions, including the open and closed positions illustrated in FIGS. 3A and 3B. In the open position (illustrated in FIG. 3A), the vent vane 204 rotates counterclockwise until it makes contact with the vent restrictor panel 200. The configuration of the open position allows fluid openings 312a, 312b, which are located in the jacket outer shell 302 near and along the vane axle 300, to be clear (at least in part) of the obstruction otherwise created by the vent vane 204. As a result, as discussed in more detail below, the internal fluid 310 is allowed to exit from the internal airspace 308 to the ambient environment outside the jacket assembly 106. The fluid openings 312a, 312b, include an inlet opening 312a and an outlet opening 312b.

In the closed position (illustrated in FIG. 3B), the vent vane 204 rotates clockwise until it makes contact with the jacket outer shell 302. The configuration of the closed position allows the obstruction (or blocking) of the fluid openings 312a, 312b and, thus, preventing further exchange of fluids between the internal airspace 308 and the ambient environment.

In other positions, the vent vane 204 is rotated sufficiently to allow partial exchange of the fluids between the internal airspace 308 and the ambient environment. For example, instead of rotating the vent vane 204 approximately 90 degrees between the open and closed positions illustrated in FIGS. 3A and 3B, the vent vane 204 is rotated only about 45 degrees, to limit the cooling effect. The partial positions are beneficial, for example, if a slower cooling effect is desired.

Figure 4A:
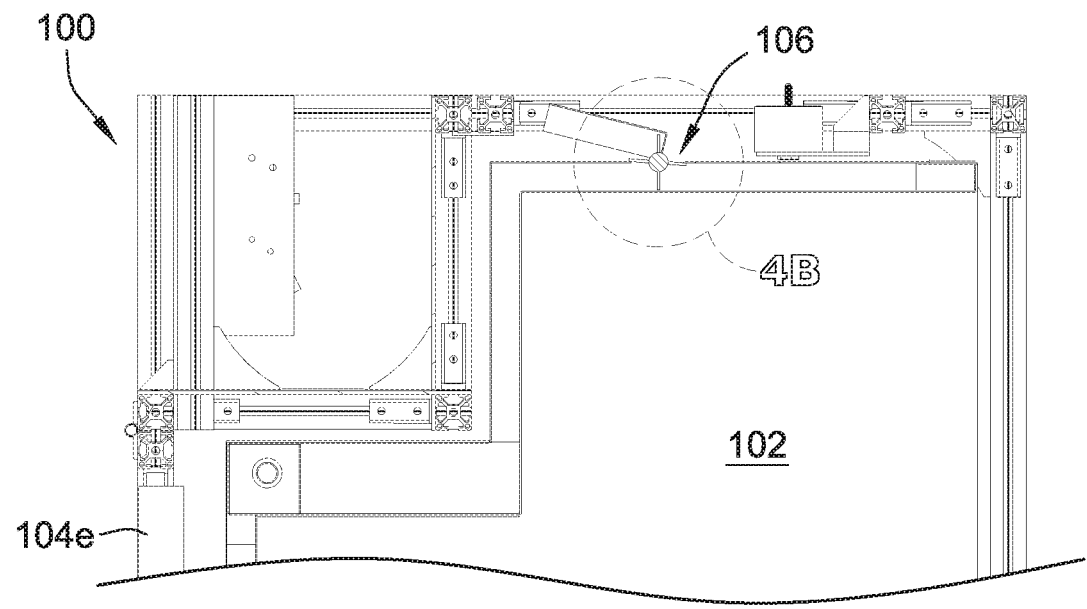
FIG. 4A is a partial cross-sectional diagrammatic view of the vent vane assembly mounted in a fluid jacket assembly.
Figure 4B:
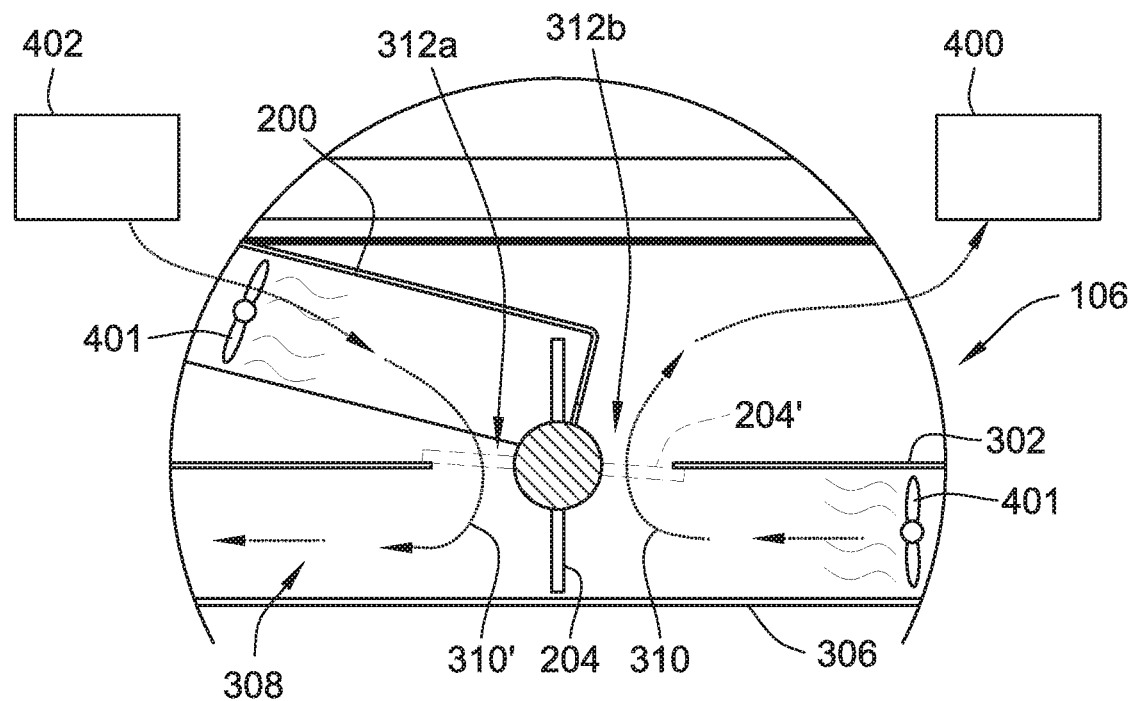
FIG. 4B is an enlarged view of the vent vane assembly of FIG. 4A.

Referring to FIGS. 4A and 4B, the flow of the internal fluid 310 is illustrated when the vent vane 204 is in the open position, with the vent vane 204 being in a generally vertical position. The closed position is also illustratively represented, with the vent vane 204' being in a generally horizontal position.

In the open position, outgoing internal fluid 310 exits through the outlet opening 312b, while incoming internal fluid 310' enters through the inlet opening 312a. The outgoing internal fluid 310 escapes to the ambient environment and/or to an outlet reservoir 400, which is an external fluid reservoir for receiving the hot fluid 310. Optionally, the outgoing internal fluid 310 is pushed by one or more fans 401 from the internal airspace 308 into the ambient environment and/or to the outlet reservoir 400. The incoming internal fluid 310' is received from the ambient environment and/or from an inlet reservoir 402, which is an external fluid reservoir in which cooled fluid is stored. Optionally, the incoming internal fluid 310' is pulled into the internal airspace 308 from the ambient environment and/or from the inlet reservoir 402 by one or more of the fans 401.

In the closed position, the internal fluid 310 circulates in the jacket assembly 106 in a loop, e.g., it continues to re-circulate until the vent vane 204 is in the open position. When the homogenous temperature $T_H$ inside the internal chamber 102 exceeds a threshold temperature, i.e., when the enclosure temperature reaches a tripping point, a controller actuates the vent vane 204 to open. According to one example, the controller is included with the drive motor 206. According to another example, the controller is separate from the drive motor 206 and is mounted internal or external to the incubator assembly 100.

Regardless, when the threshold temperature is exceeded, the controller causes the vent vane 204 to open and, thus, achieve a temperature change within the internal chamber 102. Accordingly, assuming that a cooling of the internal chamber 102 is desired, the opening of the vent vane 204 has the effect of interrupting the recirculation loop of the internal fluid 310 and pushing the warm jacketed fluid into the environment, while pulling cool air from the environment into the internal airspace 308.

The embodiment described above illustrates, generally, a rotating vent configuration. One advantage of this configuration is that a single motion produces a flow path that allows simultaneously, for example, warm air to leave the air jacket and cooler (e.g., room-temperature air) to enter the air jacket. However, other embodiments are not limited to a rotating vent configuration. By way of another example, another configuration is a sliding vent configuration in which a vent vane is mounted parallel to the outer shell such that the vent vane is slidable to cover/uncover fluid openings.

Figure 5:
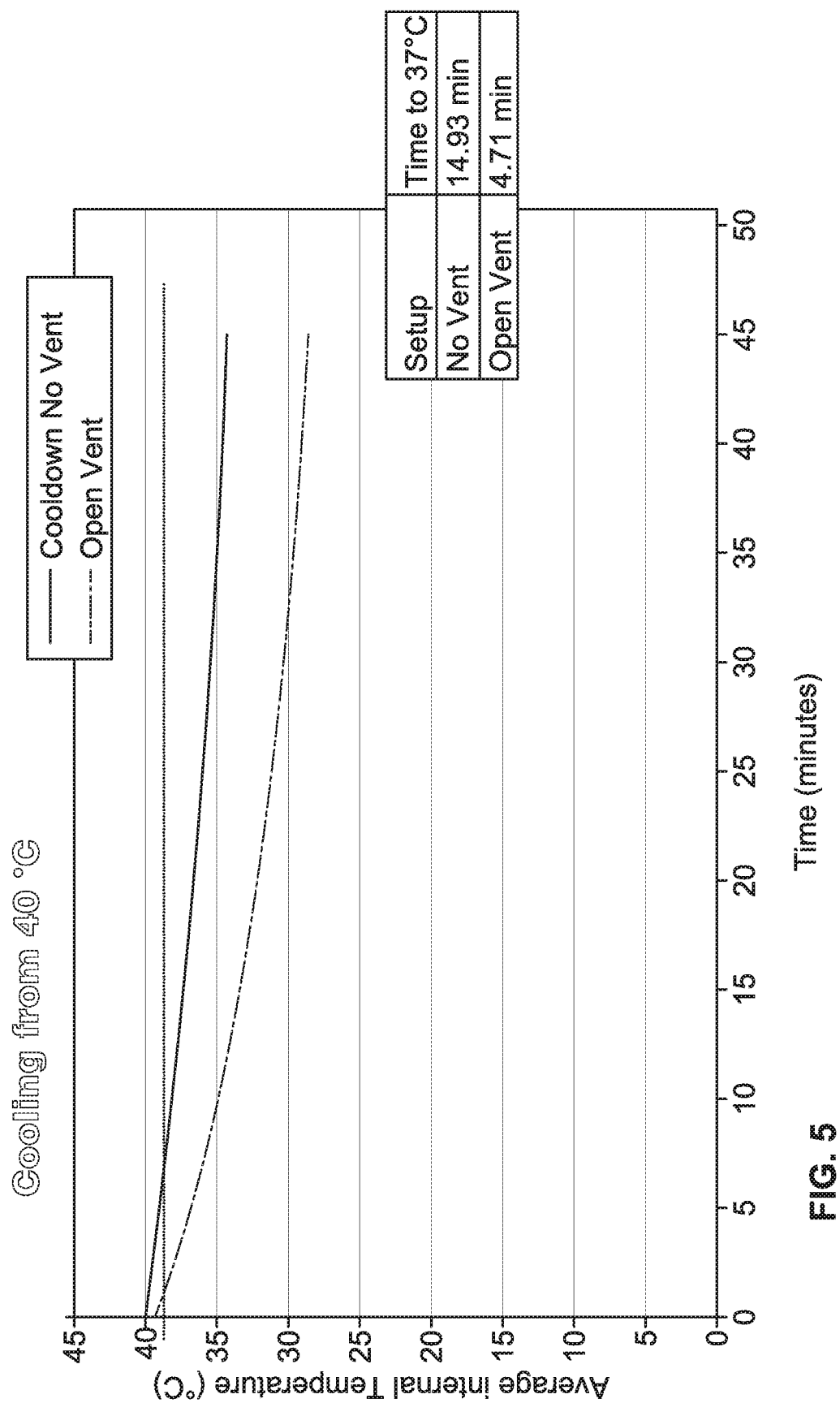
FIG. 5 is a chart with experimental data illustrating cooling temperatures inside the incubator assembly.

Referring to FIG. 5, experimental data illustrates recorded time in which an internal chamber of an incubating enclosure cooled down from 40 degrees Celsius to an average internal incubator temperature (e.g., to a desired homogeneous temperature $T_H$ of 37 degrees Celsius). The data includes a representative solid line that illustrates the cool-down time for an incubator that lacks a vent. The time for the vent-less incubator was recorded to be 14.93 minutes. The data further includes a representative broken line that illustrates the cool-down time for an incubator that includes a vent as described above (e.g., a vent with a vent vane 204). In stark contrast to the vent-less incubator, the cool-down time for the vented incubator was recorded to be 4.71 minutes—more than 10 minutes faster than the vent-less incubator. Thus, using an incubator with a vent increased the cooling time by at least about 69 percent.

Figure 6:
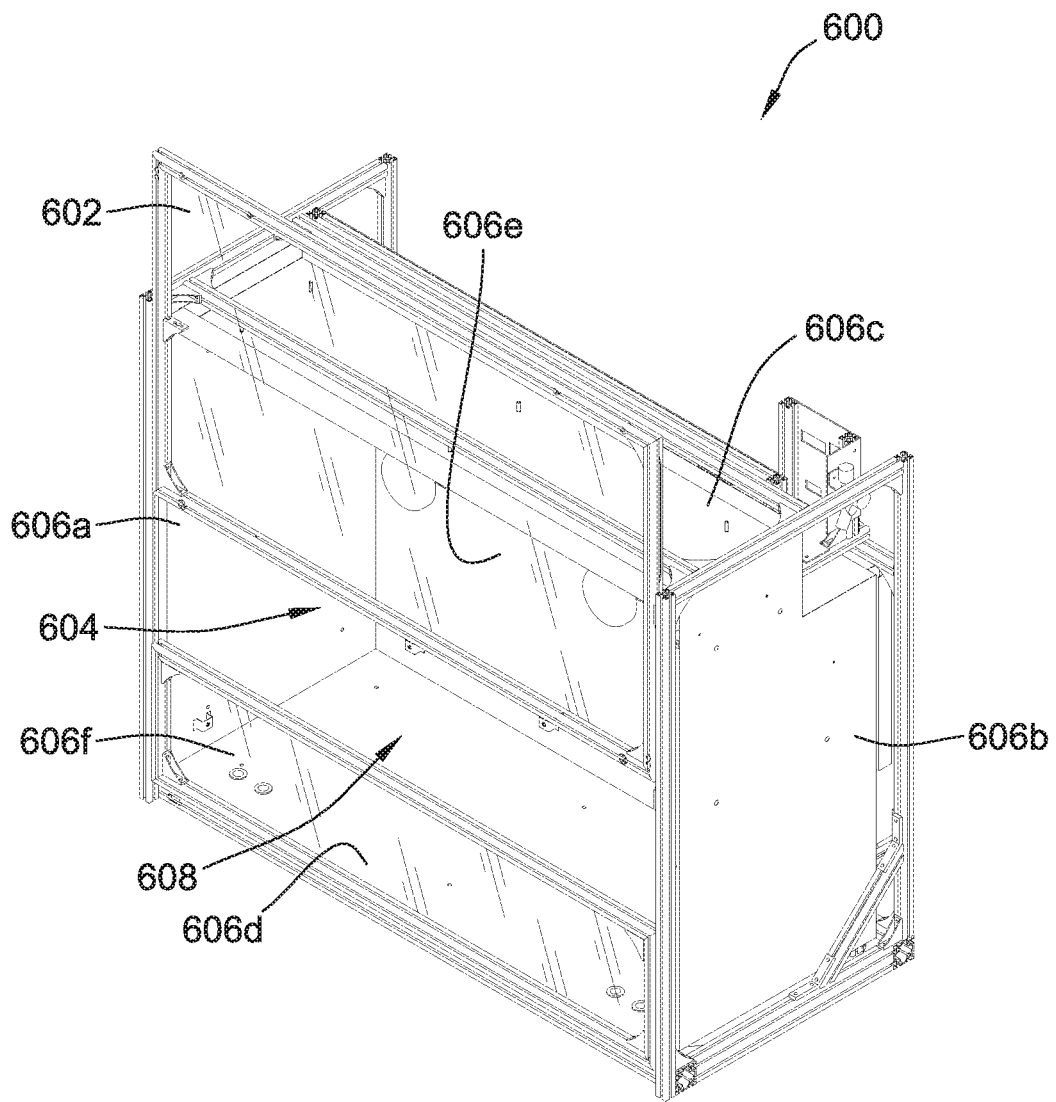
FIG. 6 is an isometric view of an incubator assembly with a movable sash.

Referring to FIG. 6, an incubator assembly 600 includes a sash 602 for providing enhanced user access to an internal chamber 604 of the incubator assembly 600. The incubator assembly 600 includes a plurality of walls, including a left wall 606a, a right wall 606b, a top wall 606c, a bottom wall 606d, a back wall 606e, and a front wall 606f. The sash 602 is mounted in a front position of the incubator assembly 600, between the left and right walls 606a, 606b, and above the front wall 606f. Optionally, the incubator assembly 600 includes a jacket assembly similar to or identical with the jacket assembly 106 described above.

The sash 602 is slidable upwards to provide a user opening 608 for accessing the internal chamber 604. As such, the sash 602 is movable between a closed position, in which the internal chamber 604 is generally sealed from contact with the ambient environment, and an open position, in which the internal chamber 604 is accessible to the user.

Referring to FIG. 7, some advantages of the sash 602 are illustrated by showing an interaction between users and the internal chamber 604. For example, the sash 602 is beneficial because it allows users 700, 702 of different heights to access elements 704 of the internal chamber 604 in a comfortable manner. In contrast to prior chambers, in which incubators have access doors that are typically positioned at uncomfortable levels (e.g., near the floor or ceiling of a laboratory) that require users to bend down or reach up, the sash 602 is positioned nominally at a user chest level to make incubator operations easy and comfortable. The illustrated users 700, 702 can vary in height, e.g., between five and seven feet, and, yet, still be able to comfortably access the elements 704 through the sash 602, which is dimensioned and shaped according to the desired specifications.

Another benefit of the sash 602 is that it protects the user's head from a cell culture region 706 in the internal chamber 604, and/or vice-versa. Moving the sash 602 upwards in the open position, basically raises the sash 602 near the user's head to provide contamination protection for the user and/or the elements 704.

Optionally, air flow 708 in the internal chamber 604 is controlled to behave in a manner that protects the users 700, 702 and/or samples within the internal chamber 604 from contamination by content of the internal chamber 604 and/or the ambient environment. For example, one or more fans 710 direct the air flow in a direction away from the user opening 608 when the user 700 is interacting with the internal chamber 604.

Figure 8A:
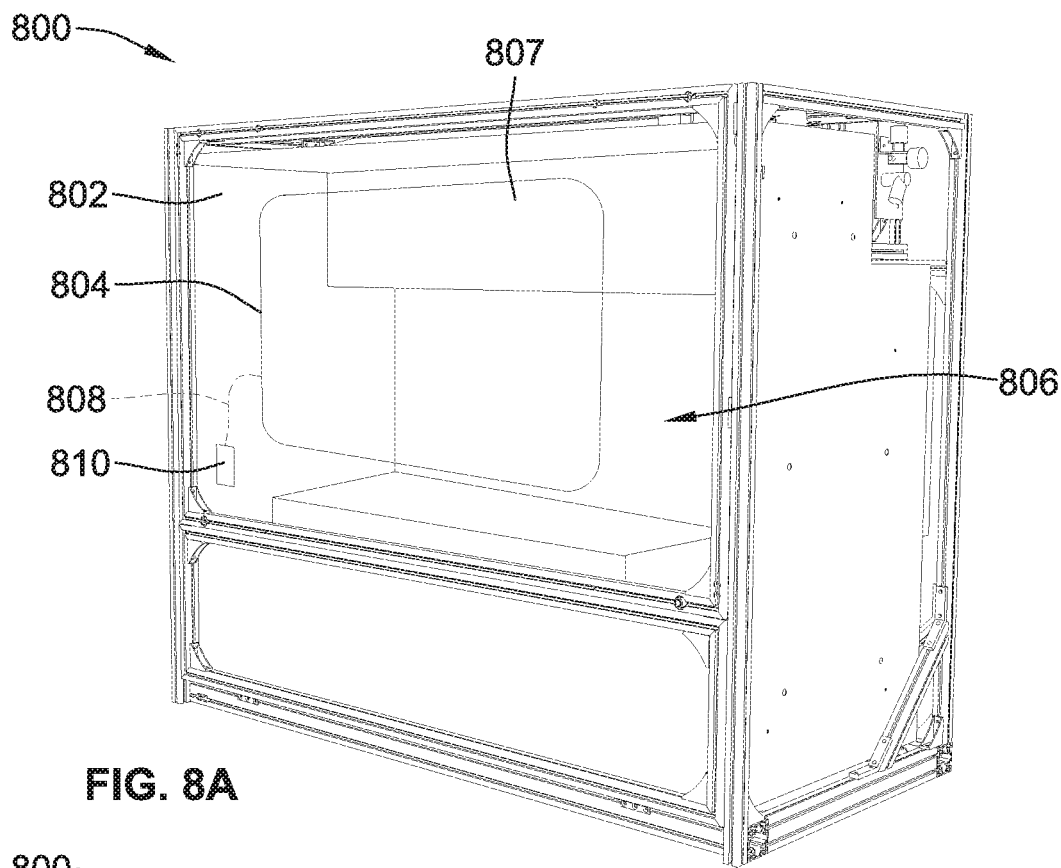
FIG. 8A illustrates a movable sash with a window tint in an activated state.
Figure 8B:
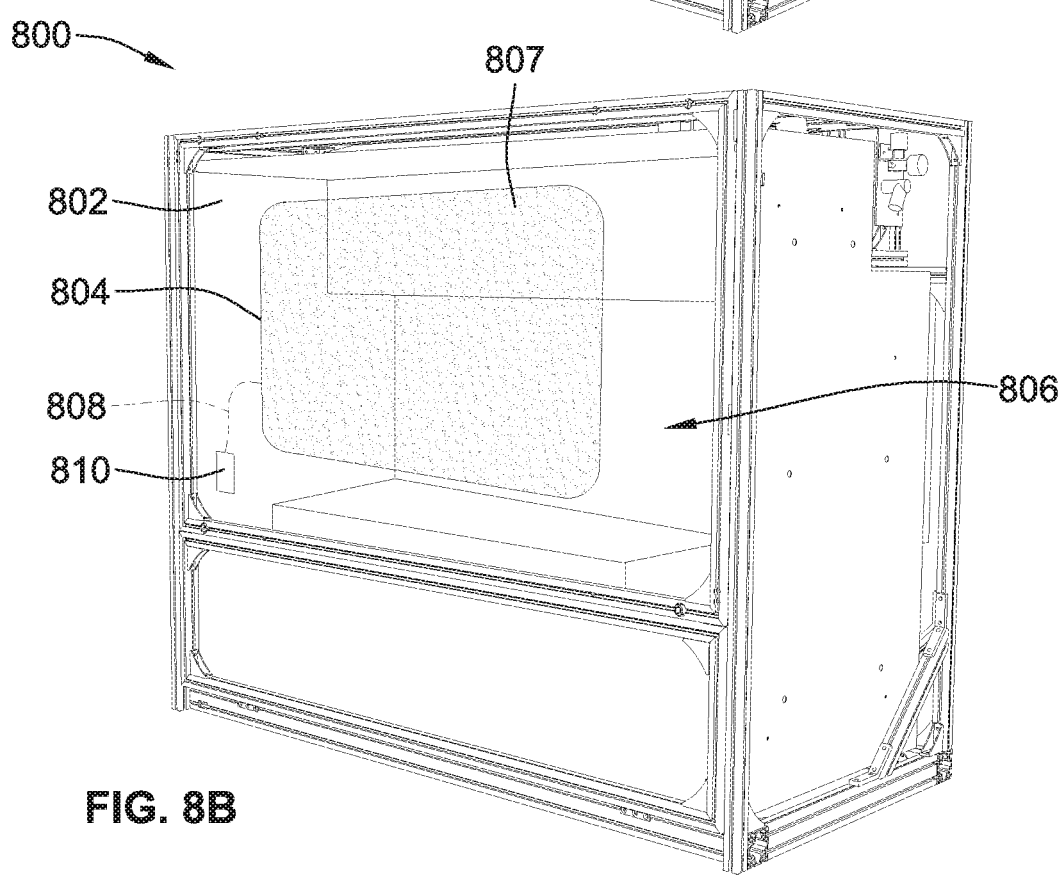
FIG. 8B illustrates the window tint of FIG. 8A in an inactivated state.

Referring to FIGS. 8A and 8B, an incubator assembly 800 includes a sash 802 having a viewing window 804 whose transparency is modulated by a user and/or through software for the purpose of protecting light-sensitive components in an internal chamber of the incubator assembly 800. The sash 802 is similar to but not necessarily identical to the sash 602 described above in reference to FIGS. 6 and 7. The viewing window 804 allows an user to see into the internal chamber 806 when the sash 802 is open and when the sash 802 is closed. In contrast to typical windows of current incubators, which allow light into the internal chamber 806 and could damage light-sensitive dyes or cells inside the internal chamber 806, the viewing window 804 includes a protective layer 807 that is controllably activated for blocking predetermined wavelengths (e.g., UV energy) from entering the internal chamber 806.

In FIG. 8A, the viewing window 804 is illustrated in a transparency mode in which, in response to a voltage being applied, the protective layer 807 allows the predetermined wavelengths (e.g., ambient light) to pass through the viewing window 804. In FIG. 8B, the viewing window 804 is illustrated in an opaque mode in which, in response to the voltage no longer being applied, the protective layer 807 blocks the predetermined wavelengths from passing through the viewing window 804. The voltage is applied or removed in response to receiving one or more signals 808 from an activated switch 810. Thus, the protective layer 807 of the viewing window 804 changes between the transparency mode and the opaque mode in response to receiving a signal 808 from an activated switch 810.

By way of a specific example, the protective layer 807 is a "smart tint" and the activated switch 810 is a button on the sash 802. The tint is ON by default and is turned OFF when a user pushes the button 810. Generally, the ON mode is a viewing mode and the OFF mode is a non-viewing mode. Optionally, the tint automatically returns to the ON state after a predetermined time period, e.g., after 30 seconds. In yet another optional embodiment, the tint is automatically turned OFF when the sash 802 is opened.

In other examples, the protective layer 807 is any layer that blocks ultraviolet light or other wavelengths that are harmful to media components. For example, the protective layer 807 includes one or more of materials selected from a group of liquid-crystal materials and/or electro-chromic materials. Optionally or alternatively, instead of or in addition to a tint, the protective layer 807 includes one or more of a mechanical shade, a shutter, an additional door, and/or transmissive liquid-crystal display (LCD) device.

In another example, instead of or in addition to a button, the switch 810 is a motion detector device that automatically activates/deactivates the protective layer 807 without physical contact between the user and the switch 810. More specifically, the protective layer 807 is automatically activated when the motion detector device 810 detects a user nearby the viewing window 804, e.g., when the user is in a motion detection zone. The protective layer 807 is, then, deactivated after a predetermined time period (e.g., 30 seconds after being activated or after no longer sensing user motion).

In one preferred by, the motion detector device 810 senses and distinguishes among various types of gestures from the operator. Each type of gesture is associated with a specific operator command (e.g., deactivating the protective layer 807, activating the protective layer 807, opening the sash, closing the sash). Accordingly, the operator is permitted to easily control access to and from the incubator assembly 800.

When the protective layer 807 includes a transmissive liquid-crystal display (LCD) device, the display can be made opaque to limit the type of light that enters into the incubator assembly 800, or transmissive to permit the into the incubator assembly 800. Additionally, because it is a display device, various regions within the display device can be used to provide information about the operation of the devices and systems within the incubator assembly 800. For example, one region can display the live temperature within the incubator assembly 800, perhaps in graph format so that the temperature profile over a period of time can be readily identified by the operator.

When the contents of the incubator assembly 800 include organ-on-chip (OOC) devices that entail the culturing and testing of various types of cells, the operation of the motors and pumps that provide fluids to the OOC devices can be displayed on the transmissive LCD (e.g., in graph format showing operation over a period of time). Additionally, because sensor devices such as temperature sensors and pressure sensors are often incorporated into those OOC devices, the outputs associated with the sensors can also be displayed on the transmissive LCD. Similarly, because the OOC devices are often used with optical and/or image sensing devices (e.g., microscopes), real-time images associated with the optical and/or image sensors can also be displayed on the transmissive LCD. Because several OOC devices may be undergoing testing within the incubator assembly, various regions of the transmissive LCD can be assigned to each of the plurality of OOC devices being tested.

Figure 9:
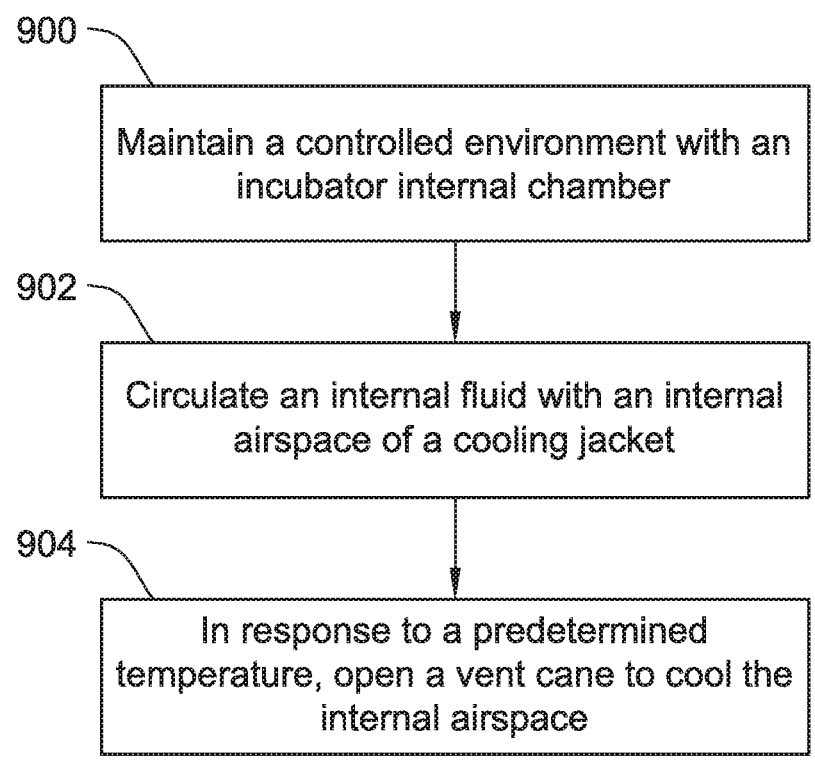
FIG. 9 is diagrammatic illustrating a method for cooling an incubator assembly.

Referring to FIG. 9, a method is directed to cooling an incubator assembly such as any of the incubator assemblies described above in reference to FIGS. 1-8B. At 900, a controlled environment is maintained within an incubator internal chamber. At 902, an internal fluid is circulated within an internal airspace of a cooling jacket to maintain a homogenous temperature within the incubator internal chamber. At 904, a vent vane is opened, in response to a predetermined temperature being reached within the incubator internal chamber, to cool the internal airspace of the cooling jacket. For example, a vent vane is moved from a closed position to an open position to allow both (a) a hot fluid to exit the internal space into an ambient environment and (b) a cold fluid to enter the internal airspace. Consequently, cooling of the controlled environment is achieved within the incubator internal chamber.

Each of these embodiments and obvious variations thereof is contemplated as falling within the spirit and scope of the claimed invention, which is set forth in the following claims. Moreover, the present concepts expressly include any and all combinations and subcombinations of the preceding elements and aspects.

What is claimed is:

1. A method for cooling an incubator assembly having an incubator enclosure with an internal chamber defined by one or more walls, the internal chamber containing devices that culture cells, tissues, or organs along with one or more devices to move fluids through said devices, the incubator assembly further having a jacket assembly mounted adjacent to at least one of the walls, the jacket including a vent vane and an internal airspace containing an internal fluid, the method comprising:
   maintaining a environment with a first temperature within the internal chamber of an incubator enclosure;
   re-circulating the internal fluid within the internal airspace of the jacket wherein the vent vane is in a closed position; and
   when the devices change the first temperature of the internal chamber to a higher, second temperature, moving the vent vane of the jacket from the closed position to an open position to allow fluid to exit the internal airspace of the jacket into an ambient environment.

2. The method of claim 1, further comprising:
   rotatably moving the vent between the closed position and the open position;
   pushing, via one or more ventilation fans, the fluid into the ambient environment; and
   pulling, via at least one of the one or more ventilation fans, the fluid into the internal airspace of the jacket.

3. The method of claim 1, further comprising automatically moving, via a controller, the vent vane between the closed position and the open position.

4. The method of claim 1, further comprising moving a sash of the incubator assembly from a closed position to an open position to access the internal chamber of the incubator enclosure.

5. The method of claim 4, further comprising, in response to a voltage being applied, changing a protective layer of the sash between a transparency mode and an opaque mode.

6. A method for cooling an incubator assembly having an incubator enclosure with an internal chamber defined by one or more walls, the chamber containing one or more devices, the incubator assembly further having a jacket assembly mounted adjacent to at least one of the walls, the jacket including a vent vane and an internal airspace containing an internal fluid, the method comprising:
   maintaining an environment within the internal chamber of the incubator enclosure;
   circulating the internal fluid within the internal airspace of the jacket with the vent vane in a closed position to maintain a first temperature within the internal chamber; and
   when the one or more devices change the temperature to a higher, second temperature, moving the vent vane of the jacket from the closed position to an open position to allow fluid to exit the internal airspace of the jacket into an ambient environment outside said assembly.

7. The method of claim 6, wherein the moving of the vent vane also allows fluid from the ambient environment to enter the internal airspace of the jacket.

8. The method of claim 6, wherein the device comprises a pump.

9. The method of claim 6, wherein the device comprises a motor.

10. The method of claim 6, wherein the device comprises a microscope.

11. The method of claim 6, wherein said chamber further contains devices for culturing cells and the one or more devices move fluid through said devices for culturing cells.

12. The method of claim 11, wherein the fluid moved through the devices for culturing cells is media.

13. A method for cooling an incubator assembly having an incubator enclosure with an internal chamber defined by one or more walls, the internal chamber containing devices that culture cells, tissues, or organs along with one or more devices to move fluids through the devices, the incubator assembly further having a jacket assembly mounted adjacent to at least one of the walls, the jacket including a vent vane and an internal airspace containing an internal fluid, the method comprising:
   maintaining an environment with a first temperature within the internal chamber of an incubator enclosure;
   re-circulating the internal fluid within the internal airspace of the jacket with the vent vane in a closed position; and
   when the one or more devices for moving fluids change the temperature of the internal chamber to a higher, second temperature, moving the vent vane of the jacket from a closed position to an open position to allow fluid to exit the internal airspace of the jacket into an ambient environment.

* * * * *